(12) United States Patent
Georgiev

(10) Patent No.: US 6,433,016 B1
(45) Date of Patent: Aug. 13, 2002

(54) DRUGS FOR TREATING VIRAL INFECTIONS

(76) Inventor: Vassil Stefanov Georgiev, 121 Kent Oaks Way, Gaithersburg, MD (US) 20878

( * ) Notice: Subject to any disclaimer, the term of this patent is extended or adjusted under 35 U.S.C. 154(b) by 0 days.

(21) Appl. No.: 09/895,377

(22) Filed: Jul. 2, 2001

Related U.S. Application Data

(60) Provisional application No. 60/260,878, filed on Jan. 12, 2001.

(51) Int. Cl.[7] .................. A61K 31/16; C07C 311/48
(52) U.S. Cl. ........................................ 514/600; 564/79
(58) Field of Search ......................... 564/79; 514/600

(56) References Cited

U.S. PATENT DOCUMENTS 4,292,305 A * 9/1981 Ali et al. .................... 424/45

* cited by examiner

*Primary Examiner*—Peter O'Sullivan

(57) ABSTRACT

A series of substituted sulfonamide derivatives have been prepared and may be used to treat antiviral infections, especially infections caused by orthopoxviruses.

28 Claims, No Drawings

DRUGS FOR TREATING VIRAL INFECTIONS

This application claims the benefit of provisional application No. 60/260,878, filed Jan. 12, 2001.

BACKGROUND OF THE INVENTION

The invention relates generally to carbocyclic imidodisulfamide derivatives and more specifically to N,N$^1$-bis[[tricyclo 3.3.1.1$^{3,7}$]dec-1-yl]alkyl]-, N,N$^1$-bis[[tricyclo [3.3.1.1$^{3,7}$]dec-$^2$-yl]alkyl]-, and N, N$^1$-di(bicyclo[2.2.1] hept-2-yl)imidodisulfamide derivatives, as well as their alkali salts and N-monophosphates. The compounds of this invention possess broad antiviral activity, especially activity against orthopoxviruses.

Ali at al., J. Med. Chem. 25: 1235–1240 (1982) describe a series of N,N$^1$-bis(arylcyclopropyl)imidodisulfamide derivatives having antiallergic activity. Appel and Helwerth, Chem. Ber. 101: 1743–1745 (1968) disclose a bis (cyclohexyl)imidodisulfamide derivative. Yamaguchi and Nakano [Japan. Patent 19,962 (1963)] disclose the ammonium salt of a bis(cyclohexyl)imidodisulfamide derivative.

SUMMARY OF THE INVENTION

In accordance with the invention, there are provided compounds of the formula:

$$[R-(CH_2)_nNHSO_2]_2NR^1 \quad (I)$$

wherein n is 0, 1 or 2, R is a carbocyclic radical selected from the group consisting of adamantyl, norbornyl, cyclooctyl and cyclododecyl, and R$^1$ is hydrogen, alkali metal such as sodium, potassium, etc., ammonium cation, and monophosphate moiety.

The invention further provides a method for treating a warm blooded animal for viral infections, preferably but not limited to infections caused by orthopoxviruses (such as vaccinia virus, cowpox, smallpox, monkeypox, camelpox, etc.) which method comprises administering to such animal an effective amount of a compound of formula (I).

DETAILED DESCRIPTION OF THE INVENTION

The compounds of the invention may be prepared by reacting an appropriate carbocyclic alkylamine derivative (1) with imidodisulfuryl chloride (2) in the presence of triethylamine (n and R are as defined above):

$$R-(CH_2)_nNH_2 + HN(SO_2Cl)_2 \longrightarrow [R-(CH_2)_nNHSO_2]_2NH$$
$$1 \quad\quad\quad 2 \quad\quad\quad\quad\quad\quad 3$$

The following carbocyclic alkylamine intermediates (1) are commercially available: tricyclo[3.3.1.1$^{3,7}$]decan-1-amine (1; R=1-adamantyl, n=0); [(tricyclo[3.3.1.1$^{3,7}$]-dec-1-yl)methyl]amine (1; R=1-adamantylmethyl, n=1); tricyclo [3.3.1.1$^{3,7}$]decan-2-amine (1;R=2-adamantyl, n=0); exo-bicyclo[2.2.1]heptan-2-amine (1; R=exo-2-norbornyl, n=0); and endo-bicyclo[2.2.1]heptan-2-amine (1; R=endo-2-norbornyl, n=0).

Tricyclo[3.3.1.1$^{3,7}$]decan-1-ethanamine (1; R=1-adamantyl, n=2) may be prepared according to U.S. Pat. No. 3,534,036 of V. L. Narayanan and F. L. Weisenborn, the entire disclosure of which is incorporated herein by reference.

Tricyclo[3.3.1.1$^{3,7}$]decan-2-ethanamide (1; R=2-adamantyl, n=2) and 2-(tricyclo[3.3.1.13,7]dec-2-ylidene) ethanamine (4)

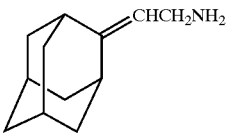

were prepared according to the procedure of Mariani et al., Il Farmaco, Ed. Sci. 31: 272 (1976) and Schenonone et al. Il Farmaco, Ed. Sci. 27: 322 (1972).

Imidodisulfuryl chloride was prepared utilizing the procedure of Appel and Eisenhouer, Chem. Ber. 95: 1753 (1962).

The compounds of the invention may also be prepared as their ammonium salts (6) by reacting an appropriate carbocyclic alkylamine derivative (1) (n and R are defined as above) with the ammonium salt of imidodisulfuryl chloride (5) according to the procedures of Appel and Helwerth [Chem. Ber. 101: 1743–1745 (1968)] and Yamaguchi and Nakano [Japan. Patent 19,962 (1963)]:

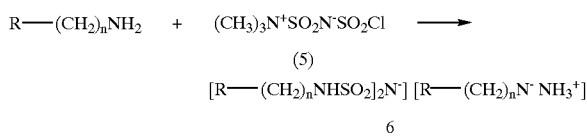

$$R-(CH_2)_nNH_2 + (CH_3)_3N^+SO_2N^-SO_2Cl \longrightarrow$$
$$(5)$$
$$[R-(CH_2)_nNHSO_2]_2N^-] [R-(CH_2)_nN^- NH_3^+]$$
$$6$$

In order to increase their solubility in water and saline, the compounds of the invention may also be prepared as their alkali salts (8) by reacting an appropriate carbocyclic imidodisulfamide derivative 3 (n and R are defined as above) with aqueous alkaline hydroxide solution such as but not limited to sodium hydroxide and potassium hydroxide:

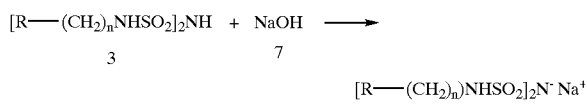

$$[R-(CH_2)_nNHSO_2]_2NH + NaOH \longrightarrow$$
$$3 \quad\quad\quad\quad\quad 7$$
$$[R-(CH_2)_n)NHSO_2]_2N^- Na^+$$
$$8$$

In order to increase their solubility in water and saline, the compounds of the invention may also be prepared as their N-substituted monophosphate derivatives (10) according to the procedure of Zavlin and Efremov, Phosphorous Sulfur, 40: 247–251 (1991) by reacting an appropriate carbocyclic imidodisulfamide derivative 3 (n and R are defined as above) with a phosphorylating agent 9 (e.g., phosphoric anhydride, phosphorus trichloride, phosphorous pentoxide and phosphorous oxychloride):

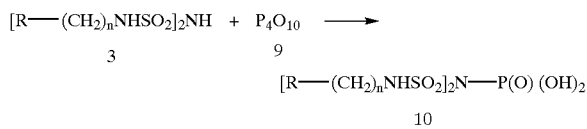

$$[R-(CH_2)_nNHSO_2]_2NH + P_4O_{10} \longrightarrow$$
$$3 \quad\quad\quad\quad\quad 9$$
$$[R-(CH_2)_nNHSO_2]_2N-P(O)(OH)_2$$
$$10$$

By having increased solubility in water and saline, compounds of the formula 6, 8 and 10 may be easily administrated by oral, intranasal, and intraperitoneal routes to treat warm-blooded animals against infections caused by orthopoxviruses.

The present invention is illustrated in more detail by reference to the following non-limiting examples.

EXAMPLE 1

N,N¹-Bis(tricyclo[3.3.1.1$^{3,7}$]dec-1-yl) imidodisulfamide (3; R=1-adamantyl, n=0)

Under a nitrogen atmosphere, triethylamine (177.71 mL, 1.275 mol) was added over 1.75 hour to a solution of imidodisulfuryl chloride (90.95 g, 0.425 mol) in 2.55 L of anhydrous acetonitrile at −40° C. (dry ice/acetone bath). The resulting yellow solution was stirred at −40° C. for 1 hour and then allowed to warm to 0° C. While stirring rapidly, solid tricyclo[3.3.1.1$^{3,7}$]decan-1-amine (192.84 g, 1.275 mol) was added portionwise over 2 hours at such a rate that allowed the temperature of the reaction mixture to be maintained at −5 to 0° C. for 1 hour, and at room temperature for 18 hours, the insolubles were filtered off and the filtrate evaporated under reduced pressure. The resulting residue and the insolubles were combined and dissolved in 2 L of methanol. The methanolic solution was acidified with 2 equivalents of 2 N hydrochloric acid (490 L), and stirred at ambient temperature for 30 min. After dilution with 2.5. L of water, a precipitate formed. The reaction mixture was filtered off and the crude solid was recrystallized from ethanol providing 105.4 g of white crystalline compound 3 (R=1-adamantyl, n=0). M.p. 210° C. (decomp.).

Anal. Calcd. For $C_{20}H_{33}N_3O_4S_2$: C, 54.15; H, 7.50; N, 9.47; S, 14.45. Found: C, 54.00; H, 7.52; N; 9.55; S, 14.54.

EXAMPLE 2

Exo-N,N¹-Bis(bicyclo[2.2.1]hept-2-yl) imidodisulfamide (3; R=2-norbornyl, n=0)

The compound of the example was prepared by a procedure similar to that described in Example 1 except that exo-bicyclo[2.2.1]heptan-2-amine (1; R=exo-2-norbornyl, n=0) was substituted for tricyclo[3.3.1.1$^{3,7}$]-decan-1-amine. M.p. 208° C. (ethanol).

Anal. Calcd. For $C_{14}H_{25}N_3O_4S_2$: C, 46.26; H, 6.93; N, 11.56; S, 17.64. Found: C, 46.22; H, 6.96; N, 11.51; S, 17.71.

EXAMPLE 3

Endo-N,N¹-Bis (bicyclo[2.2.1]hept-2-yl) imidodisulfamide (3; R=2-norbornyl, n=0)

The compound of this example was prepared by a procedure similar to that described in Example 1 except that endo-bicyclo[2.2.1]heptan-2-amine (1; R=endo-2-norbornyl, n=0) was substituted for tricyclo[3.3.1.1$^{3,7}$]-decan-1-amine, and 5 moles of triethylamine were used instead of 3 moles. M.p. 205–206° C. (ethanol).

Anal. Calcd. For $C_{14}H_{25}N_3O_4S_2$: C, 46.26; H, 6.93; N, 11.56; S, 17.64. Found: C, 46.21; H, 6.94; N, 11.54; S, 17.63.

EXAMPLE 4

N,N¹-Bis[2-(tricyclo[3.3.1.1$^{3,7}$]-dec-1-yl)ethyl] imidodisulfamide (3; R=1-adamantyl, n=2)

The compound of the example was prepared by a procedure similar to that described in Example 1 except that [2-(tricyclo[3.3.1.1$^{3,7}$]dec-1-yl)ethyl]amine (1; R=1-adamantyl, n=2) was substituted for tricyclo[3.3.1.1$^{3,7}$]-decan-1-amine. M.p. 162–164° C. (ethanol).

Anal. Calcd. For $C_{24}H_{41}N_3O_4S_2$: C, 57.68; H, 8.27; N, 8.41; S, 12.83. Found: C, 57.54; H, 8.30; N, 8.32; S, 12.84.

EXAMPLE 5

N,N¹-Bis (tricyclo[3.3.1.1$^{3,7}$]dec-1-yl)methyl] imidodisulfamide (3; R=1-adamantyl, n=1)

The compound of this example was prepared by a procedure similar to that described in Example 1 except that [(tricyclo[3.3.1.1$^{3,7}$]dec-1-yl)methyl]amine (1; R=1-adamantyl, n=1) was substituted for tricyclo[3.3.1.1$^{3,7}$]-decan-1-amine. M.p. 187–190° C. (ethanol).

Anal. Calcd. For $C_{22}H_{37}N_3O_4S_2$: C, 56.02; H, 7.91; N, 8.91; S, 13.59. Found: C, 55.74; H, 8.25; N, 8.83; S, 13.25.

EXAMPLE 6

N,N¹Bis[2-(tricyclo[3.3.1.1$^{3,7}$]dec-2-yl)ethyl] imidodisulfamide (3; R=2-adamantyl, n=2)

The compound of this example was prepared by a procedure similar to that described in Example 1 except that [2(tricyclo[3.3.1.1$^{3,7}$]des-2-yl)ethyl]amine (1; R=2-adamantyl, n=2) was substituted for tricyclo[3.3.1.1$^{3,7}$]-decan-1-amine. M.P. 180–181° C. (ethanol).

Anal. Calcd. For $C_{24}H_{41}N_3O_4S_2$: C, 57.68; H, 8.27; N, 8.41; S, 12.83. Found: C, 57.79; H, 66; N, 8.40; S, 12.80.

EXAMPLE 7

N,N¹-Bis[2-[(tricyclo[3.3.1.1$^{3,7}$]dec-2-yl)ethyl] imidodisulfamide (11)

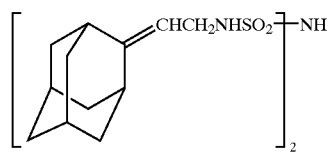

The compound of this example was prepared by a procedure similar to that described in Example 1 except that 2-(tricyclo[3.3.1.1$^{3,7}$]dec-2-ylidene)ethanamine (4) was substituted for tricyclo[3.3.1.1$^{3,7}$]decan-1-amine. M.p. 182–183° C. (ethanol).

Anal. Calcd. For $C_{24}H_{37}N_3O_4S_2$: C, 58.15; H, 7.52; N, 8.48; S, 12.94. Found: C, 58.30; H, 7.58; N, 8.48; S, 12.75.

EXAMPLE 8

N,N¹-Di(tricyclo[3.3.1.1$^{3,7}$]dec-2-yl) imidodisulfamide (3; R=2-adamantyl, n=0)

The compound of this example was prepared by a procedure similar to that described in Example 1 except that tricyclo[3.3.1.1$^{3,7}$]decan-2-amine (1; R=2-adamantyl, n=0) was substituted for tricyclo[3.3.1.1$^{3,7}$]decan-1-amine and 5 moles of triethylamine were used instead of 3 moles. M.p. 221–222° C. (decomp.) (2-propanol).

Anal. Calcd. For $C_{20}H_{33}N_3O_4S_2$: C, 54.15; H, 7.50; N, 9.47; S, 14.45. Found: C, 54.62; H, 7.74; N, 9.50; S, 14.06.

EXAMPLE 9

N,N¹-Dicyclooctylimidodisulfamide (3; R= cyclooctyl, n=0)

The compound of the example was prepared by a procedure similar to that described in Example 1 except that cyclooctylamine (1; R=cyclooctyl, n=0) was substituted for tricyclo[3.3.1.1$^{3,7}$]decan-1-amine. M.p. 183–185° C. (ethanol).

Anal. Calcd. for $C_{16}H_{33}N_3O_4S_2$: C, 48.58; H, 8.41; N, 10.62; S, 16.21. Found: C, 48.77; H, 8.78; N, 10.54; S, 15.86.

EXAMPLE 10

N,N$^1$-Dicyclododecylimidodisulfamide (3; R= cyclododecyl, n=0)

The compound of this example was prepared by a procedure similar to that described in Example 1 except that cyclododecylamine (1; R=cyclododecyl, n=0) was substituted for tricyclo[3.3.1.1$^{3,7}$]decan-1-amine. M.p. 205° C. (ethanol).

Anal. Calcd. For $C_{24}H_{49}N_3O_4S_2$: C, 56.77; H, 9.73; N, 8.28; S, 12.63. Found: C, 56.62; H, 9.60; N, 8.28; S, 12.26.

EXAMPLE 11

Sodium N,N$_1$ (tricyclo[3.3.1.1$^{3,7}$ dec-1-yl) imidodisulfamide (1; R=1-adamantyl, n=0, R$^1$= sodium)

N,N$^1$-Bis(tricyclo[3.3.1.1$^{3,7}$]dec-1-yl)imidodisulfamide (200 mg) was suspended in 5 mL of absolute methanol. Then, 1.5 mL of 10 percent aqueous sodium hydroxide solution was added and the reaction mixture was heated slightly in water bath until complete dissolution of the imidodisulfamide 3 (R=1-adamantyl, n=0). After cooling, the resulting sodium salt precipitated as white fluffy crystalline mass. The solvent was stripped under vacuum leaving 200 mg of the sodium salt of 1 (R=1-adamantyl, n=0, R$^1$=sodium). M.p. over 200° C. (water).

EXAMPLE 12

N,N$^1$ (tricyclo[3.3.1.1$^{3,7}$ dec-1-yl)imidodisulfamide Monophosphate (1; R=1-adamantyl, n=0, R$^1$=P(O) (OH)$_2$)

N,N$^1$-Bis (tricyclo [3.3.1.1$^{3,7}$]dec-1-yl)imidodisulfamide (200 mg; 36 mmol) and 51 mg of phosphoric anhydride (P$_4$O$_{10}$; 18 mmol) were heated in trichloromethane (10 mL; distilled from phosphoric anhydride) overnight. After evaporation of the solvent, the residue was saturated repeatedly with diethyl ether until the reaction product was obtained as powder. M.p. over 200° C.

Antiviral Activity

The antiviral activity of the compounds of the invention was determined by several methods through the National Institute of Allergy and Infectious Diseases, NIH Testing Program.

According to the method of Sidwell et al. Appl. Microbiol. 22: 747–801, antiviral activity is determined by using viral cytopathogenic effect (CPE) inhibition in 96-well microplates. Seven concentrations (1,000, 320, 100, 32, 10, 3.2, and 1.0 microgram/mL final concentration in panel cups) of compounds were employed. Compound was added to the cells to be infected 15 minutes before virus exposure. A virus dosage equivalent to the CCID50 was then administered. (The virus concentration which causes 50% cell death, established by titration of a cell monolayer with a homogenate of cultures from 100 virally infected cells). Antiviral activity may be expressed as virus rating (VR) in accordance with Sidwell et al., and as a minimum inhibitory concentration (MIC). Cytotoxicity of each dosage level of compound was evaluated in the same plate using microscopically visible cell anomalies as criterion for evaluation. Included with each test was a known positive compound—ribavirin, sodofovir (HPMPC) and/or cyclic HPMPC may be used as positive controls for RNA viruses. The antiviral test was read approximately 72 hours after addition of virus, at the time when viral CPE reached essentially maximal levels.

In the plaque reduction assay using cowpox virus in cell culture, the compounds of the invention were applied both during and after virus adsorption in order to determine whether compounds were acting as inhibitors of virus adsorption as opposed to an intracellular mode of action. Confluent 6-well plates of monkey(Vero) cells were used. For compound being present during the virus adsorption process, cell medium was aspirated and 2× compound was applied followed by virus diluted to give about 100 plaque forming units (PFU) per well. Compound and virus containing medium were each in a volume of 0.2 mL. Plates were rocked every 5–10 minutes for an hour, after which time the medium was removed and 2.0 mL of 1× compound in MEM/2% Fetal Bovine Serum was applied for three days. For compound being present after the virus adsorption period, 100 PFU of virus per 0.4 mL was rocked on cells for an hour as described above. After that time, the medium was removed and 2.0 mL of 1× compound in MEM/2% fetal Bovine Serum was applied per well for three days. Wells were aspirated and covered with about 1.0 mL/well of 0.1% crystal violet in 10% buffered formalin for 5 minutes. Then, plates were aspirated, rinsed under tap water, and blotted dry. A light box was used to aid in counting the plaques in each well. Sidofovir (HPMPC) and cyclic HPMPC were used as positive controls.

In the cytopathic effect inhibition assay, low passage (3–10) human foreskin fibroblast (HFF) cells are trypsinized, counted, and seeded into 96-well tissue culture plates at a cell concentration of 2.5×10$^4$ cells in 0.1 mL of minimal essential medium (MEM) supplemented with 10% fetal bovine serum (FBS). The cells are then incubated for 24 hours at 37° C. in a 5% CO$_2$:95% air, 90% humidified atmosphere. The media is then removed and 100 microliter of MEM containing 2% FBS is added to all but the first row. In the first row, 125 microliter of media containing the compound is added in triplicate wells. Media alone is added to both cell and virus control wells. The compound in the first row of wells is then diluted serially 1:5 throughout the remaining wells by transferring 25 microliter using the Cetus Liquid Handling Machine. The plates are then incubated for 60 minutes and 100 microliter of an appropriate virus concentration added to each well, excluding cell control wells, which received 100 microliter of MEM. In initial experiments, the virus concentration utilized will be 1,000 Plaque Forming Units (PFU) per well. The plates are then incubated at 37° C. in a CO$_2$ incubator for five days. After the incubation period, media is aspirated and the cells stained with a 0.1% crystal violet solution for four days. The stain is then removed and the plates rinsed using tap water until all excess stain is removed. The plates are allowed to dry for 24 hours, and the amount of CPE in each row determined using a BioTek Multiplate Autoreader. EC50 and IC50 values are determined by comparing compound-treated and compound-untreated cells using a computer program. (The EC50 value measures compound concentration that inhibits viral replication by 50%; the IC50 value detects compound toxicity to dividing cells by measuring compound concentration that inhibits cell growth by 50%).

In the plaque reduction assay, two days prior to use, HFF cells are plated into six well plates and incubated at 37° C. with 5% CO$_2$ and 90% humidity. On the date of the assay, the compound is made up at 2× the desired concentration in 2×MEM with 5% FBS and then serially diluted 1:5 using six concentrations of compound. The initial concentration is 200 microgram/mL. The compound dilutions are then placed in a 42° C. water bath. The 4% agarose for the overlay is prepared with reagent quality water and microwaved until the agarose has dissolved. This is then placed into the 42° C. water bath to cool. The virus to be used is diluted in MEM containing 10% FBS to a desired concentration, which will give 20–30 plaques per well. The media is then aspirated from the wells and 0.2 microliter of virus is added to each well in triplicate with 0.2 microliter of media being added to compound toxicity wells. The plates are then incubated for one hour with shaking every 15 minutes. After incubation, an equal amount of agarose is added to each compound dilution. Each agarose/compound dilution is then added to the appropriate wells. The assay is incubated for five days, after which the cells are stained with 2.0 microliter per well of 5% neutral red stain for six hours. The stain is then aspirated, and the plaques counted using a stereomicroscope at 10× magnification.

In the cowpox virus plaque assay, in one condition the compound of Example 1 was added to cells 5 minutes before virus adsorption and then continuously for 3 days. In the second condition, virus was adsorbed first for 1 hour, then the compound was added for three days. The compound of Example 1 was found to be equally active under both conditions with an EC50 value in monkey (Vero) cells of 2.0 microgram/mL. At 3.0 microgram/mL, the plaques were nearly completely eliminated, and at 1.0 microgram/mL the plaques were tiny relative to the untreated ones. Cell monolayers were healthy up to 30 microgram/mL (the highest concentration tested). From previous data, sidofovir (HPMPC) is active in these cells at about 12.0 microgram microgram/mL.

In the CPE inhibition assay, the compound of Example 1 showed the following values measuring anti-orthopoxvirus activities:

(A) Vaccinia Virus (HFF Cells)

EC50:0.05 microgram/mL;

EC90: 1.40 microgram/mL;

CC50: 77.80 microgram/mL;

DV50: 2.20 microgram/mL;

SI: 1,556

(B) Cowpox Virus (HFF Cells)

EC50:1.10 microgram/mL;

EC90: 7.30 microgram/mL;

CC50: 77.80 microgram/mL;

CDV50: 3.80 microgram/mL;

CDV90:13.30 microgram/mL;

SI: 77.8

(CC50 measures the cytotoxic concentration in uninfected cells; The Selectivity Index (SI) measures the compound toxicity and is calculated according to CC50/EC50).

In the plaque reduction assay, the compound of Example 1 showed the following values measuring anti-orthopoxvirus activities:

(A) Vaccinia Virus (HFF Cells)

EC50:0.09 microgram/mL;

EC90: 0.15 microgram/ml;

CC50: 100.00 microgram/mL;

CDV50: 50.90 microgram/mL;

CDV90: 19.9 microgram/mL;

SI: 1,111

(B) Cowpox Virus (HFF Cells)

EC50: 0.49 microgram/mL;

EC90: 1.70 microgram/mL;

CC50: 100.0 microgram/mL;

CDV50: 11.70 microgram/mL; CDV90: 18.7 microgram/mL

SI: 204

When tested in the CPE assay against nine variola virus (smallpox) isolates (eight major, and one minor), the compound of Example 1 showed an average EC50 of 0.10 microgram/mL, and CC50 of 43.0 microgram/mL.

In the Neutral Red Uptake Assay (using stationary HFF cells), the compound of Example 1 showed the following values measuring toxicity:

CC50: 78.9 microgram/mL;

ACV CC50: over 100 microgram/mL;

In the CPE inhibition assay, the compound of Example 11 showed the following values measuring anti-orthopoxvirus activities:

(A) Vaccinia Virus (HFF Cells)

EC50:0.04 microgram/mL;

EC90: 0.11 microgram/ML

CC50: 65.00 microgram/mL;

CDV EC50: 1.80 microgram/mL;

CDV EC90: 3.7 microgram/mL

SI: 1,625

(B) Cowpox Virus (HFF Cells)

EC50: 0.50 microgram/mL;

EC90: 2.10 microgram/mL

CC50: 65.00 microgram/mL;

CDV EC50: 2.30 microgram/mL

CDV EC90: 3.90 microgram/mL

SI: 130

(CC50 measures the cytotoxic concentration in uninfected cells; The Selectivity Index (SI) measures compound toxicity and is calculated according to CC50/EC50).

In the plaque reduction assay, the compound of Example 11 showed the following values measuring anti-orthopoxvirus activities:

(A) Vaccinia Virus (HFF Cells)

CC50: 87.60 microgram/mL

In the Neutral Red Uptake Assay (using stationary HFF cells), the compound of Example 11 showed the following values measuring toxicity:

CC50: 87.6 microgram/mL;

ACV CC50: over 100 microgram/mL;

CDV CC50: over 100 microgram/mL

When tested against cowpox infection in female BALB/c mice, an intraperitoneal dose of 100 mg/kg daily of the compound of Example 11 given twice daily for 5 days starting 4 hours before virus challenge significantly reduced the virus titer on Day 3 of measurement as follows:

Lung titer on Day 3: 6.6±1.3 ($P<0.05$)

Saline: 8.0±0.2

For pharmaceutical purposes, the compounds of this invention can be administered to warm-blooded animals perorally, parenterally, topically or intranasally as active ingredients in customary dosage unit compositions. These dosage unit compositions contain the active ingredient and at least one inert pharmaceutical carrier. Dosage unit forms contemplated by the present invention include tablets, capsules, solutions, suspensions, aerosols, and parenteral compositions such as intramuscular, intravenous or intradermal preparations. Sustained release dosage forms are also contemplated where the active ingredient is bound to an exchange resin that, optionally, can be coated with a diffusion barrier coating to modify the release properties of the resin.

The quantity of active ingredient administered in such dosage forms can vary over a wide range depending upon the mode of administration, the size and weight of the patient and whether the nature of the treatment is prophylactic or therapeutic in nature. In general, dosage unit forms containing from about 1.0 mg to 250 mg of the active ingredient. In humans, the dose is administered from 1 to 4 times daily. The total daily dosage will be from about 5.0 mg to 1,000 mg, although lower or higher amounts can be used. A preferred total daily dose would be from 10 mg to 100 mg of active ingredient. Pharmaceutical carriers or excipients used in the preparation of pharmaceutical compositions for use in the invention may be either organic or inorganic, solid or liquid in nature. Suitable solid excipients include gelatin, microcrystalline cellulose, lactose, starches, and magnesium sulfate. Suitable liquid excipients include water and alcohols such as ethanol, benzyl alcohol and polyethylene glycols. The preferred liquid excipients for injectable preparations include water, saline solution, dextrose solution and glycol solutions such as aqueous propylene glycol or aqueous polyethylene glycol. The properties of the formulations may be enhanced by the addition of one or more adjuvants possessing properties as viscosity enhancers, surfactans, pH modifiers, preservatives, sweeteners, stability enhancers, coloring agents, suspending agents, granulating agents, coating agents, desintegration modifiers, propellants, emulsifying agents and humectants.

The compounds of this invention may be utilized in the form of alkali metal salts. Such salts may be formed by treating the compounds with aqueous alkaline hydroxide solution such as but not limited to sodium hydroxide and potassium hydroxide.

The compounds of this invention may also be utilized in the form of N-substituted monophosphates. Such derivatives may be formed by treating the compounds 1 with phosphorylating agent such as but not limited to phosphoryl oxychloride, phosphorus trichloride.

The present invention may be embodied in other specific forms without departing from the spirit or essential attributes thereof and, accordingly, reference should be made to te appended claims, rather than to the foregoing specifications, as indicating the scope of the invention.

What is claimed is:

1. A compound having a formula

[R—(CH$_2$)$_n$NHSO$_2$]$_2$NR$^1$  (I)

wherein n is 0, 1 or 2, and R is a carbocyclic radical selected from the group consisting of adamantyl, norbornyl, cyclooctyl and cyclododocyl and R$^1$ is hydrogen, alkali metal ammonium, and a monophosphate moiety.

2. N,N$^1$-Bis(tricyclo[3.3.1.1$^{3,7}$]dec-1-yl) imidodisulfamide, a compound according to claim 1.
3. exo-N,N$^1$-Bis(bicyclo[2.2.1]hept-2-yl) imidodisulfamide, a compound according to claim 1.
4. endo-N,N$^1$-Bis(bicyclo[2.2.1]hept-2-yl) imidodisulfamide, a compound according to claim 1.
5. N,N$^1$-Bis[2-(tricyclo[3.3.1.1$^{3,7}$]dec-1-yl)ethyl] imidodisulfamide, a compound according to claim 1.
6. N,N$^1$-Bis[(tricyclo[3.3.1.1$^{3,7}$]dec-1-yl)methyl] imidodisulfamide, a compound according to claim 1.
7. N,N$^1$-Bis[2-(tricyclo[3.3.1.1$^{3,7}$]dec-2-yl)ethyl] imidodisulfamide, a compound according to claim 1.
8. N,N$^1$-Bis[2-(tricyclo[3.3.1.1$^{3,7}$]dec-2-ylidene)ethyl] imidodisulfamide, a compound according to claim 1.
9. N,N$^1$-Di(tricyclo[3.3.1.1$^{3,7}$]dec-2-yl) imidodisulfamide, a compound according to claim 1.
10. N,N$^1$-Dicyclooctylimidodisulfamide, a compound according to claim 1.
11. N,N$^1$-Dicyclododecylimidodisulfamide, a compound according to claim 1.
12. N,N$^1$-Bis(tricyclo[3.3.1.1$^{3,7}$]dec-1-yl) imidodisulfamide sodium salt (R$^1$=Na), a compound according to claim 1.
13. N,N$^1$-Bis(tricyclo[3.3.1.1$^{3,7}$]dec-1-yl) imidodisulfamide monophosphate [R$^1$=P(O) (OH)$_2$], a compound according to claim 1.
14. A method for treating a warm-blooded animal for infections caused by orthopoxviruses, which comprises administering to such animal an effective amount of a compound according to claim 1.
15. A method according to claim 14 wherein the compound is N,N$^1$-bis(tricyclo[3.3.1.1$^{3,7}$]dec-1-yl) imidodisulfamide.
16. A method according to claim 14 wherein the compound is exo-N,N$^1$-bis(bicyclo[2.2.1]hept-2-yl) imidodisulfamide.
17. A method according to claim 14 wherein the compound is endo-N,N$^1$-bis(bicyclo[2.2.1]hept-2-yl) imidodisulfamide.
18. A method according to claim 14 wherein the compound is N,N$^1$-bis[2-(tricyclo[3.3.1.1$^{3,7}$]dec-1-yl)ethyl] imidodisulfamide.
19. A method according to claim 14 wherein the compound is N,N$^1$-bis[(tricyclo[3.3.1.1$^{3,7}$]dec-1-yl)methyl] imidodisulfamide.
20. A method according to claim 14 wherein the compound is N,N$^1$-bis[2-(tricyclo[3.3.1.1$^{3,7}$]dec-2-yl)ethyl] imidodisulfamide.
21. A method according to claim 14 wherein the compound is N,N$^1$-bis[2-(tricyclo[3.3.1.1$^{3,7}$]dec-2-ylidene) ethyl]imidodisulfamide.
22. A method according to claim 14 wherein the compound is N,N$^1$-di(tricyclo[3.3.1.1$^{3,7}$]dec-2-yl) imidodisulfamide.
23. A method according to claim 14 wherein the compound is N,N$^1$-dicyclooctylimidodisulfamide.
24. A method according to claim 14 wherein the compound is N,N$^1$-dicyclododecylimidodisulfamide.
25. A method according to claim 14 wherein the compound is N,N$^1$-bis(tricyclo[3.3.1.1$^{3,7}$]dec-1-yl) imidodisulfamide sodium salt (R$^1$=Na).
26. A process for preparing a compound of the formula

[R—(CH$_2$)$_n$NHSO$_2$]$_2$NH comprising reacting a compound of the formula R—(CH$_2$)$_n$NH$_2$ with HN(SO$_2$Cl)$_2$ in the presence of triethylamine, wherein n is 0, 1 or 2, and R is a carbocyclic radical selected from the group consisting of adamantyl, norbornyl, cyclooctyl and cyclododecyl.

27. A process for preparing a compound of the formula

[R—(CH$_2$)$_n$NHSO$_2$]$_2$N$^-$Me$^+$ comprising reacting a compound of the formula [R—(CH$_2$)$_n$NHSO$_2$]$_2$NH with aqueous alkaline hydroxide solution wherein n is 0, 1 or 2, R is a carbocyclic radical selected from the group consisting of adamantyl, norbornyl, cyclooctyl and cyclododecyl, and Me is alkaline metal.

28. A process for preparing a compound of the formula $$[R\text{—}(CH_2)_n NHSO_2]_2 N\text{—}P(O)(OH)_2$$

comprising reacting a compound of the formula $[R\text{—}(CH_2)_n NHSO_2]_2 NH$ with a phosphorylating agent an organic solvent wherein n is 0, 1 or 2, and R is a carbocyclic radical selected from the group consisting of adamantyl, norbornyl, cyclooctyl and cyclododecyl.

* * * * *